Figure 1:
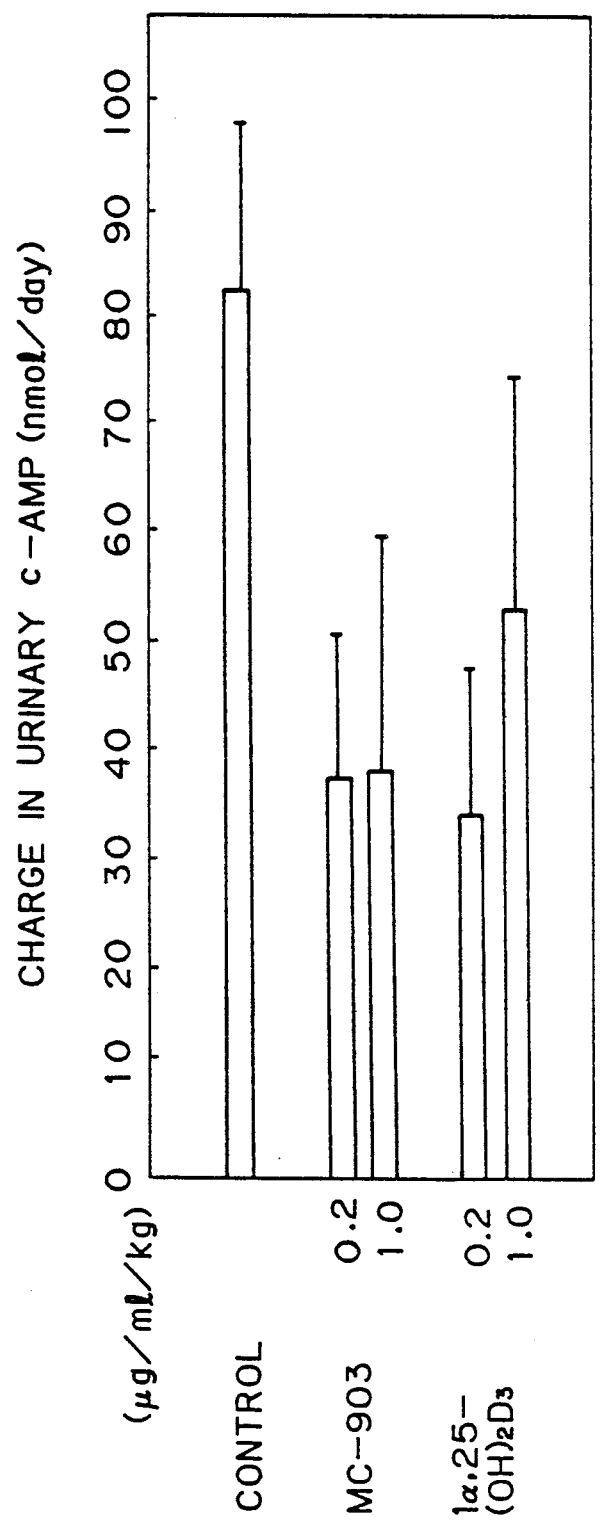

United States Patent [19]

Nishii et al.

[11] Patent Number: 5,063,221
[45] Date of Patent: Nov. 5, 1991

[54] TREATMENT FOR HYPERPARATHYROIDISM WITH USE OF VITAMIN D DERIVATIVES

[75] Inventors: Yasuho Nishii, Tokyo; Yumiko Takita, Mitaka, both of Japan

[73] Assignee: Chugai Seiyaku Kabushiki Kaisha, Tokyo, Japan

[21] Appl. No.: 501,226

[22] Filed: Mar. 29, 1990

[30] Foreign Application Priority Data

Apr. 5, 1989 [JP] Japan ................. 1-87380

[51] Int. Cl.$^5$ .................. A01N 45/00; C07J 172/00; C07J 175/00
[52] U.S. Cl. ........................ 514/167; 552/653
[58] Field of Search ............ 514/167; 552/653

[56] References Cited

U.S. PATENT DOCUMENTS 4,230,701 10/1980 Holick et al. ............ 514/167
4,812,304 3/1989 Anderson et al. ........ 424/112
4,948,789 8/1990 Slatopolsky ............. 514/167

FOREIGN PATENT DOCUMENTS 101210 10/1979 Japan .
141324 2/1983 Japan .

Primary Examiner—Frederick E. Waddell
Assistant Examiner—T. J. Criares
Attorney, Agent, or Firm—Browdy and Neimark

[57] ABSTRACT

A treatment for hyperparathyroidism with use of a 1α-hydroxyvitamin D derivative of the formula (I)

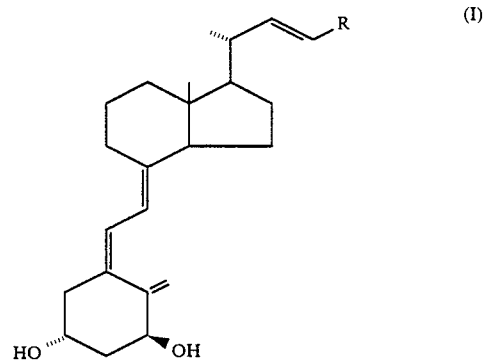

wherein R is a branched alkyl group having 4–6 carbon atoms that is substituted by one or two hydroxyl groups or a cyclopropylhydroxymethyl group, are disclosed. A pharmaceutical composition comprising the above derivatives is useful as a therapeutic agent for hyperparathyroidism such as secondary hyperparathyroidism.

11 Claims, 1 Drawing Sheet

TREATMENT FOR HYPERPARATHYROIDISM WITH USE OF VITAMIN D DERIVATIVES

This invention relates to a treatment for hyperparathyroidism with use of a 1α-hydroxyvitamin D derivative of the formula (I)

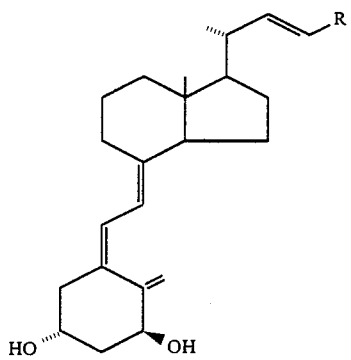

wherein R is a branched alkyl group having 4–6 carbon atoms that is substituted by one or two hydroxyl groups or a cyclopropylhydroxymethyl group.

Hyperparathyroidism, in particular, secondary hyperparathyroidism, is a disease that occurs frequently in patients undergoing renal dialysis. It has been reported that 1α,25-dihydroxyvitamin $D_3$ which is vitamin $D_3$ in the active form is an effective therapeutic agent for this disease (J. Clin. Invest., 74: 2136–3143, 1984).

Hyperparathyroidism is characterized by abnormal potentiation of parathyroid hormone (PTH) resulting from its enhanced secretion. It has been held that 1α,25-dihydroxyvitamin $D_3$ is effective against this disease because it is capable of increasing the blood calcium level. In other words, PTH is secreted in response to the decrease in the level of calcium in blood. On the other hand, PTH promotes the biosynthesis of 1α,25-hydroxyvitamin $D_3$ in the kidney. As a result, it has been postulated that 1α,25-dihydroxyvitamin $D_3$ increases the blood calcium level triggering a negative feedback system to reduce the secretion of PTH.

Currently, 1α,25-dihydroxyvitamin $D_3$ is commonly used as a therapeutic for hyperparathyroidism in patients with renal diseases. However, 1α,25-dihydroxyvitamin $D_3$ has such a great ability to raise the blood calcium level that it can cause hypercalcemia if used continuously.

The present inventors conducted intensive studies on vitamin D compounds that could be used as therapeutics for hyperparathyroidism and found that some of those vitamin D compounds which had comparatively weak or almost negligible effects on blood calcium were effective in suppressing the secretion of PTH by significant amounts. The compounds represented by the general formula (I) have weak effects on the level of calcium in blood but their ability to induce differentiation of bone marrow leukemia cells is substantially comparable to or greater than that of 1α,25-dihydroxyvitamin $D_3$ by a factor of up to 10. The relationship between vitamin D derivatives that are highly effective in increasing the level of calcium in blood, say, 1α,25-dihydroxyvitamin $D_3$, and their suppressive action on PTH secretion has been discussed in several papers but the fact that the secretion of PTH can be suppressed even by vitamin D derivatives such as the compounds of the general formula (I) that have comparatively weak effects on the level of blood calcium may well be called a new observation that has not been described in the literature. The compounds of the general formula (I) have the additional advantage that they will not cause hypercalcemia if used continuously.

The accompanying drawing illustrates the ability of compounds of the general formula (I) to suppress PTH secretion.

The compounds represented by the general formula (I) can be used in the present invention for the purpose of treating hyperparathyroidism. Specific examples of the compounds included within the scope of this general formula are those which have the chemical structures shown below by (a)–(e):

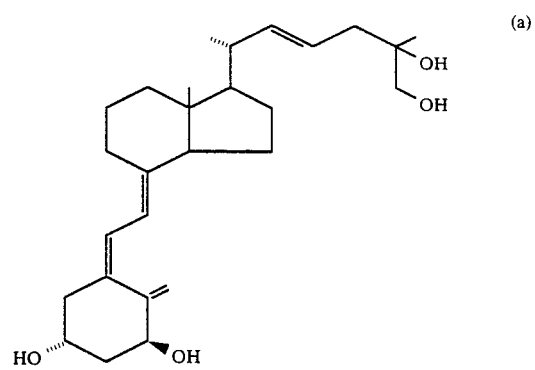

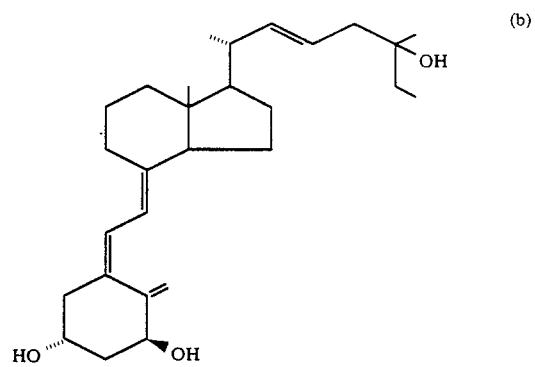

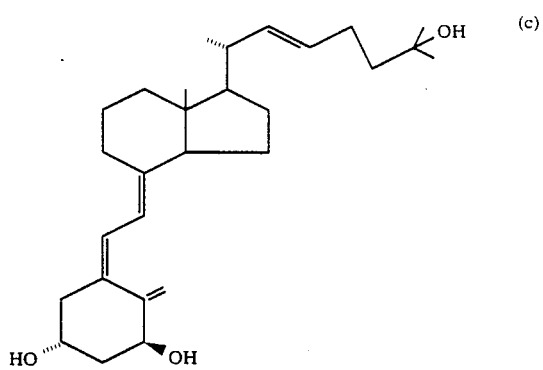

-continued

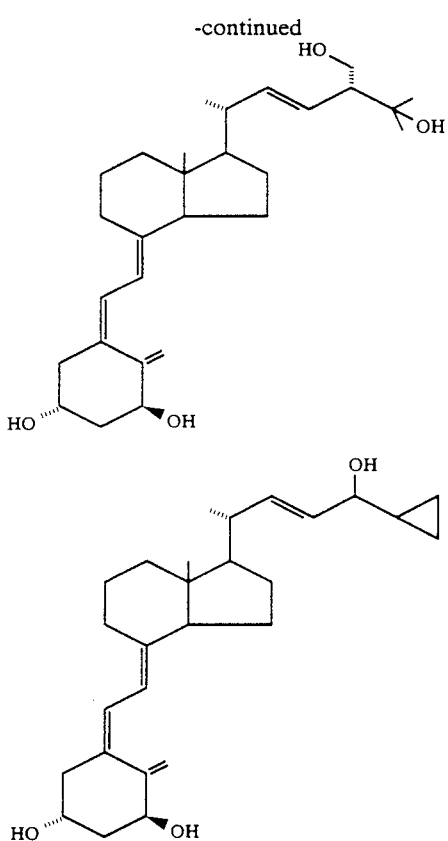

The compounds to be used in the present invention are characterized structurally by the general formula (I). In terms of biological activity, they are characterized by the following two facts: in an in vitro experimental system, their ability to induce differentiation of bone marrow leukemia cell lines such as HL-60 cell line is substantially comparable to or greater than that of 1α,25-dihydroxyvitamin $D_3$ by a factor of up to about 10; second, these compounds have almost negligible effects on the serum level of calcium or if they have, the effect is weak compared to 1α,25-dihydroxyvitamin $D_3$.

The compounds listed above having the chemical structures (a)–(e) are known and can be prepared by the methods described in prior patents such as Japanese Patent Public Disclosure No. 60-248664, Japanese Patent Domestic Announcement Nos. 62-500301, 62-501505 and 63-500661 which correspond to European Patent Publication Nos. 154,185 and 197,949 and U.S. Pat. Nos. 4,717,721 and 4,866,048, respectively.

The term "hyperparathyroidism" as used herein means a disease characterized by abnormal potentiation of PTH resulting from its enhanced secretion. Therapeutic agents containing the compounds of the general formula (I) as the active ingredient are effective in treating hyperparathyroidism, in particular, secondary hyperparathyroidism as a complication of renal diseases such as renal insufficiency.

In the treatment of secondary hyperparathyroidism, the compounds of the general formula (I) are administered either orally or parenterally (i.v.) The dose may be properly selected in accordance with the specific route of administration; for intravenous injection, it is in the range of 0.01–10 μg per injection, and for oral administration, it is in the range of 0.01–10 μg per day.

The compounds of the general formula (I) may be formulated in a desired dosage form in accordance with the specific route of administration. For oral administration, they are typically formulated in capsules or tablets. Since the dose is very small, the compounds of the general formula (I) are preferably formulated as soft capsules after being dissolved in vegetable oils or triglycerides of aliphatic acids.

An experiment conducted to investigate the ability of compounds (I) to suppress PTH depression is described below and but it should be understood that the present invention is by no means limited by this example.

EXPERIMENT (i) Animal: Purchased SD/Jcl male rats (40–45 g, 3-weeks) were fed on a 0.003% Ca/D-deficient diet for 16 days.

(ii) Drug: MC-903, or compound (I) having the chemical structure represented by (e), was used as a solution in propylene glycol. The comparative drug was 1α,25-dihydroxyvitamin $D_3$, and the control was propylene glycol.

(iii) Method: The drugs and vehicle described in (ii) were administered intraperitoneally into the animals described in (i). After 24 hours, the animals were kept in a metabolic cage for 24 hours and the urine samples were collected. The urinary level of c-AMP (index of PTH suppression) was measured by the RIA method with an assay kit of Yamasa. The results are shown in the accompanying drawing.

(iv) Results: As the drawing shows, MC-903 reduced the urinary c-AMP to a level comparable to that achieved by the comparative drug, 1α,25-dihydroxyvitamin $D_3$ [α,25-$(OH)_2D_3$]. This was due to the suppression of PTH secretion into blood.

What is claimed is:

1. A method for treating hyperparathyroidism comprising administering to a patient suffering from hyperparathyroidism an effective amount of a 1α-hydroxyvitamin D derivative of formula (I):

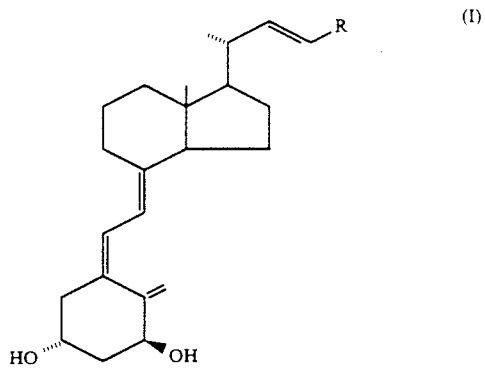

wherein R is a branched alkyl group having 4–6 carbon atoms that is substituted by one or two hydroxyl groups or a cyclopropylhydroxymethyl group.

2. A method according to claim 1 wherein a patient suffers from secondary hyperparathyroidism.

3. A method according to claim 1 wherein the derivative is administered orally.

4. A method according to claim 3 wherein the derivative is administered orally in an amount of 0.01 μg to 10 μg daily.

5. A method according to claim 1 wherein the derivative is administered intravenously.

6. A method according to claim 5 wherein the derivative is administered intravenously in an amount of 0.01 μg to 10 μg per injection.

7. A method according to claim 1 wherein the derivative has the formula (a):

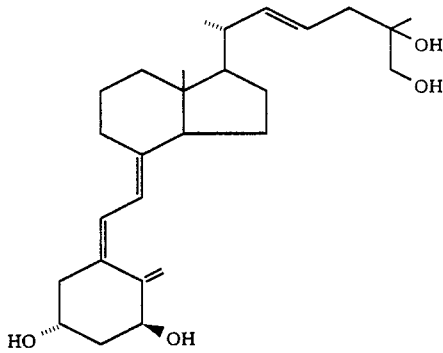
(a)

8. A method according to claim 1 wherein the derivative has the formula (b):

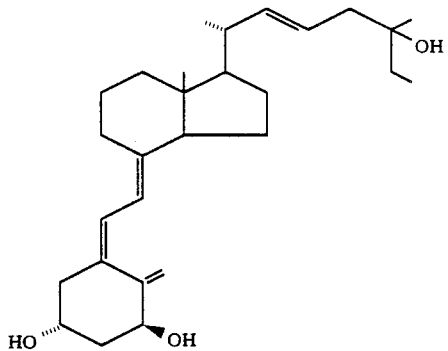
(b)

9. A method according to claim 1 wherein the derivative has the formula (c):

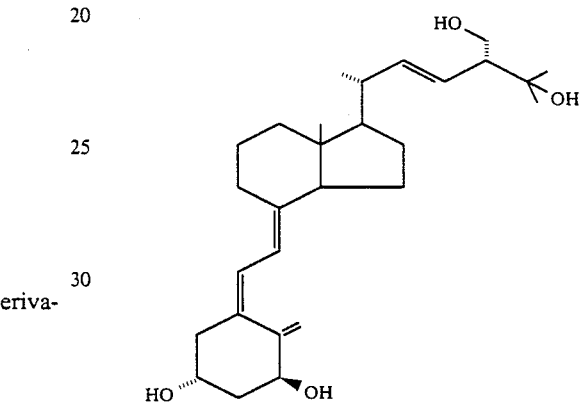
(c)

10. A method according to claim 1 wherein the derivative has the formula (d):

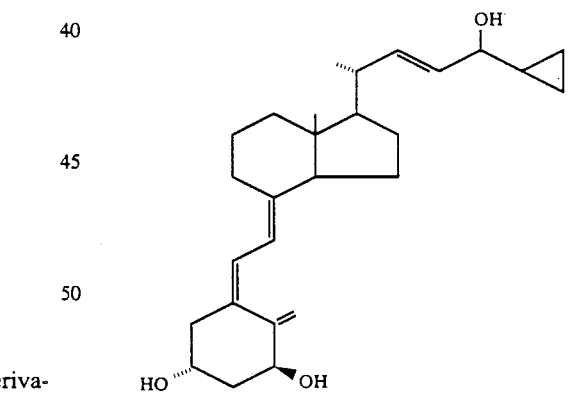
(d)

11. A method according to claim 1 wherein the derivative has the formula (e):

(e)

* * * * *